(12) United States Patent
Arramon et al.

(10) Patent No.: US 11,344,428 B2
(45) Date of Patent: *May 31, 2022

(54) INTERVERTEBRAL PROSTHESIS

(71) Applicant: Simplify Medical Pty Ltd, Paddington (AU)

(72) Inventors: Yves Arramon, Sunnyvale, CA (US); David Hovda, Mountain View, CA (US)

(73) Assignee: Simplify Medical Pty Ltd, Melbourne (AU)

( * ) Notice: Subject to any disclaimer, the term of this patent is extended or adjusted under 35 U.S.C. 154(b) by 21 days.

This patent is subject to a terminal disclaimer.

(21) Appl. No.: 16/560,847

(22) Filed: Sep. 4, 2019

(65) Prior Publication Data
US 2019/0388236 A1    Dec. 26, 2019

Related U.S. Application Data

(63) Continuation of application No. 15/842,663, filed on Dec. 14, 2017, now Pat. No. 10,426,628.

(51) Int. Cl.
*A61F 2/44* (2006.01)
*A61F 2/30* (2006.01)

(52) U.S. Cl.
CPC ...... *A61F 2/4425* (2013.01); *A61F 2002/302* (2013.01); *A61F 2002/30227* (2013.01); *A61F 2002/30616* (2013.01); *A61F 2002/30836* (2013.01); *A61F 2002/30884* (2013.01); *A61F 2002/30904* (2013.01); *A61F 2002/443* (2013.01); *A61F 2220/0025* (2013.01)

(58) Field of Classification Search
CPC .......... A61F 2/4425; A61F 2/442; A61F 2/44; A61F 2002/443
See application file for complete search history.

(56) References Cited

U.S. PATENT DOCUMENTS

| | | | |
|---|---|---|---|
| 4,997,432 A | 3/1991 | Keller et al. | |
| 5,370,697 A | 12/1994 | Baumgartner et al. | |
| 5,401,269 A | 3/1995 | Buettner-Janz et al. | |
| 5,893,889 A * | 4/1999 | Harrington | A61F 2/4425 623/17.16 |
| 6,682,562 B2 | 1/2004 | Viart et al. | |
| 7,004,971 B2 * | 2/2006 | Serhan | A61F 2/442 623/17.16 |

(Continued)

OTHER PUBLICATIONS

"International Search Report and Written Opinion for PCT/AU2019/000253 dated Mar. 26, 2019".

*Primary Examiner* — Julianna N Harvey
(74) *Attorney, Agent, or Firm* — Hoffman Warnick LLC

(57) ABSTRACT

An intervertebral prosthesis for insertion between adjacent vertebrae includes an upper plate, a lower plate and a core. The core is retained between the upper and lower plates by a retention feature in the form of central projections on the plates and a corresponding opening in the core. The retention feature is designed to allow the plates to slide over the upper and lower surfaces of the core in the anterior/posterior direction and in the lateral direction and to allow the plates to rotate with respect to each other and the core. The retention feature is also designed to prevent contact between the first and second plates during sliding movement of the plates over the core.

9 Claims, 6 Drawing Sheets

(56) References Cited

U.S. PATENT DOCUMENTS

| | | |
|---|---|---|
| 7,169,181 B2 | 1/2007 | Kuras et al. |
| 7,244,273 B2 | 7/2007 | Pedersen et al. |
| 7,442,211 B2 | 10/2008 | De Villiers et al. |
| 7,531,001 B2 | 5/2009 | De Villiers et al. |
| 7,575,599 B2 | 8/2009 | Villiers et al. |
| 7,641,692 B2 | 1/2010 | Bryan et al. |
| 7,753,956 B2 | 7/2010 | De Villiers et al. |
| 7,837,739 B2 | 11/2010 | Ogilvie et al. |
| 7,909,876 B2 | 3/2011 | Dooris et al. |
| 7,959,678 B2 | 6/2011 | Filippi et al. |
| 8,052,754 B2 | 11/2011 | Froehlich et al. |
| 8,545,564 B2 | 10/2013 | Errico et al. |
| 8,764,833 B2 | 7/2014 | De Villiers et al. |
| 8,906,033 B2 | 12/2014 | Dimauro et al. |
| 8,911,498 B2 | 12/2014 | Bartish, Jr. et al. |
| 9,011,544 B2 | 4/2015 | Arramon et al. |
| 9,101,485 B2 | 8/2015 | Berger et al. |
| 9,308,100 B2 | 4/2016 | Buettner-Janz et al. |
| 9,408,711 B2 | 8/2016 | Burkinshaw et al. |
| 10,426,628 B2 | 10/2019 | Arramon et al. |
| 2002/0035400 A1 | 3/2002 | Bryan et al. |
| 2003/0135277 A1* | 7/2003 | Bryan .................. A61F 2/4425 623/17.12 |
| 2005/0251262 A1* | 11/2005 | De Villiers ......... A61F 2/30771 623/17.14 |
| 2005/0261772 A1* | 11/2005 | Filippi .................. A61F 2/4425 623/17.13 |
| 2007/0100454 A1 | 5/2007 | Burgess et al. |
| 2011/0035010 A1* | 2/2011 | Harrington ........... A61F 2/4425 623/17.16 |
| 2013/0204369 A1 | 8/2013 | Duggal et al. |

* cited by examiner

INTERVERTEBRAL PROSTHESIS

CROSS-REFERENCE TO RELATED APPLICATIONS

The present application is a continuation of U.S. patent application Ser. No. 15/842,663, filed Dec. 14, 2017, now U.S. Pat. No. 10,426,628, the entire content of which is incorporated herein by reference.

BACKGROUND OF THE INVENTION

1. Field of the Invention

The present invention relates to medical devices and methods. More specifically, the invention relates to intervertebral prosthetic discs and methods for retaining a core in an intervertebral prosthetic disc.

Back pain takes an enormous toll on the health and productivity of people around the world. According to the American Academy of Orthopedic Surgeons, approximately 80 percent of Americans will experience back pain at some time in their life. On any one day, it is estimated that 5% of the working population in America is disabled by back pain.

Common causes of back pain are injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

When a damaged intervertebral disc causes a patient pain and discomfort, surgery is often required. Typically, surgical procedures for treating intervertebral discs involve discectomy (partial or total removal of a disc), often followed by interbody fusion of the superior and inferior vertebrae adjacent to the disc or implantation of an intervertebral prosthetic disc. Fusion is most commonly achieved by implantation of a cage or spacer together with bone graft material to promote bone growth to fuse the adjacent vertebrae together. Oftentimes, pins, rods, screws, cages and/or the like are placed between the vertebrae to act as support structures to hold the vertebrae and bone graft material in place while the bones permanently fuse together.

While such fusion procedures have been very successful for many patients, it some cases the fusion spacers or cages can be difficult to implant, and the bone regrowth necessary to achieve complete fusion can take an excessive period of time. Additionally, fusion procedures limit patient mobility. Several types of intervertebral disc prostheses are currently available. For example, one type of intervertebral disc prosthesis is the CHARITÉ™ Artificial Disc which was the first disc approved for disc replacement use in the general population of back pain patients in the U.S. This prosthesis includes upper and lower prosthesis plates or shells which locate against and engage the adjacent vertebral bodies, and a low friction core between the plates. The core has upper and lower convexly curved surfaces and the plates have corresponding, concavely curved recesses which cooperate with the curved surfaces of the core. This allows the plates to slide over the core to allow required spinal movements to take place. The curved recesses in the plates are surrounded by annular ridges which locate, at the limit of sliding movement of the plates over the core, in opposing upwardly and downwardly facing, peripheral channels surrounding the curved surfaces of the core.

This type of disc configuration is described in U.S. Pat. No. 5,401,269. A drawback of such configurations is that because the core is in effect merely "clamped" between the plates, this configuration does not allow for secure retention of the core. In one alternative arrangement, the curved surfaces of the core carry opposing, elongate keys that locate in elongate grooves in the plates and another alternative arrangement in which the plates have opposing elongate keys that locate in elongate grooves in the opposite curved surfaces of the core. These key and groove arrangements allow the plates to slide over the core within the limits of the length of the grooves, in one direction only. Although allowance is made for some lateral play of the keys in the grooves, very little sliding movement of the plates over the core can take place in the orthogonal vertical plane, and this is considered to be a serious drawback of this design. Other currently available intervertebral disc prostheses have similar and/or other drawbacks. Typically, drawbacks include insufficient resistance to wear and tear, restricted range of motion, undesirable contact between plates causing potential wear, excessive disc height not appropriately matched to patient anatomy and/or insufficient ability of the prosthesis to adhere to vertebral bone.

Therefore, a need exists for improved intervertebral disc prostheses. Ideally, such improved prostheses would resist wear and tear, provide a desired range of motion, provide a low height and adhere well to vertebral bone. At least some of these objectives will be met by the present invention. At least some of these objectives will be met by the inventions described herein below.

2. Description of the Background Art

A variety of intervertebral disc designs are described in described in U.S. Pat. Nos. 7,531,001; 7,442,211; 7,753,956; 7,575,599; 8,764,833 and 9,011,544.

BRIEF SUMMARY OF THE INVENTION

The present invention provides alternative and improved apparatus and methods for performing intervertebral disc replacement procedures.

In accordance with one embodiment, an intervertebral prosthesis for insertion between adjacent vertebrae includes a first plate, a second plate and a core. The first plate has an outer surface locatable against a respective vertebrae, an inner curved surface, an annular perimeter surrounding the inner curved surface and a lateral portion between the annular perimeter surface and the outer surface. A first central projection extends from the inner curved surface of the first plate. The second plate has an outer surface locatable against a respective vertebrae, an inner curved surface, an annular perimeter surface surrounding the inner curved surface and a lateral portion between the annular perimeter and the outer surface. A second central projection extends from the inner curved surface of the second plate toward the first plate. The core has upper and lower curved surfaces complementary in shape to the inner, curved surfaces of the first and second plates to allow the plates to slide over the upper and lower surfaces of the core and a central opening for receiving the first and second central projections. The first and second central projections and central opening cooperate with one another to retain the core between the plates and limit motion of the first and second plate with respect to one another to prevent contact between the annular perimeter surfaces of the first and second plates during sliding movement of the plates over the core. The first and second central projections each have a diameter of about one half or less of a diameter of the central opening in the core.

In accordance with another embodiment, an intervertebral prosthesis for insertion between adjacent vertebrae includes a first plate, a second plate and a core. The first plate has an outer vertebral contacting surface, an inner bearing surface and a central projection extending from the inner bearing surface. The second plate has an outer vertebral contacting surface, an inner bearing surface and a central projection extending from the inner bearing surface toward the first plate. The core has upper and lower curved surfaces complementary in shape to the inner, bearing surfaces of the first and second plates to allow the plates to slide over the upper and lower surfaces of the core and a central opening for receiving the central projections of the first and second plates. The first and second central projections and central opening cooperate with one another to retain the core between the plates and to prevent contact between any portion of the first and second plates during sliding movement of the plates over the core. The first and second plates are capable of articulating with respect to one another about the core at least 5 degrees and no more than 8 degrees from a neutral position in each of the anterior/posterior and lateral directions.

In accordance with further embodiment, a method of retaining a core in an intervertebral prosthetic disc includes steps of providing a first plate having an outer vertebral contacting surface, an inner bearing surface and a central projection extending from the inner bearing surface; providing a second plate having an outer vertebral contacting surface, an inner bearing surface and a central projection extending from the inner bearing surface toward the first plate; and providing a core between the first and second plates. The core has upper and lower curved surfaces complementary in shape to the inner, bearing surfaces of the first and second plates to allow the plates to slide over the upper and lower surfaces of the core and a central opening for receiving the central projections of the first and second plates. The core is retained between the plates and contact is prevented between the plates during sliding movement of the plates over the core by cooperation of the first and second central projections and central opening when the intervertebral prosthetic disc is in an assembled configuration. The first and second plates are allowed to articulating about the core at least 5 degrees and no more than 8 degrees from a neutral position in each of the anterior/posterior and lateral directions in the assembled configuration.

According to another embodiment, a method of preventing contact between plates in an intervertebral prosthetic disc, the method comprising:
providing a first plate having an outer vertebral contacting surface, an inner bearing surface and a central projection extending from the inner bearing surface;
providing a second plate having an outer vertebral contacting surface, an inner bearing surface and a central projection extending from the inner bearing surface toward the first plate;
providing a core between the first and second plates, the core having upper and lower curved surfaces complementary in shape to the inner, bearing surfaces of the first and second plates to allow the plates to slide over the upper and lower surfaces of the core and a central opening for receiving the central projections of the first and second plates;

preventing contact between the plates during sliding movement of the plates over the core by cooperation of the first and second central projections and central opening when the intervertebral prosthetic disc is in an assembled configuration; and
allowing the first and second plates to articulating about the core at least 5 degrees from a neutral position in each of the anterior/posterior and lateral directions in the assembled configuration, wherein the first and second central projections each have a diameter of about one half or less of a diameter of the central opening in the core.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
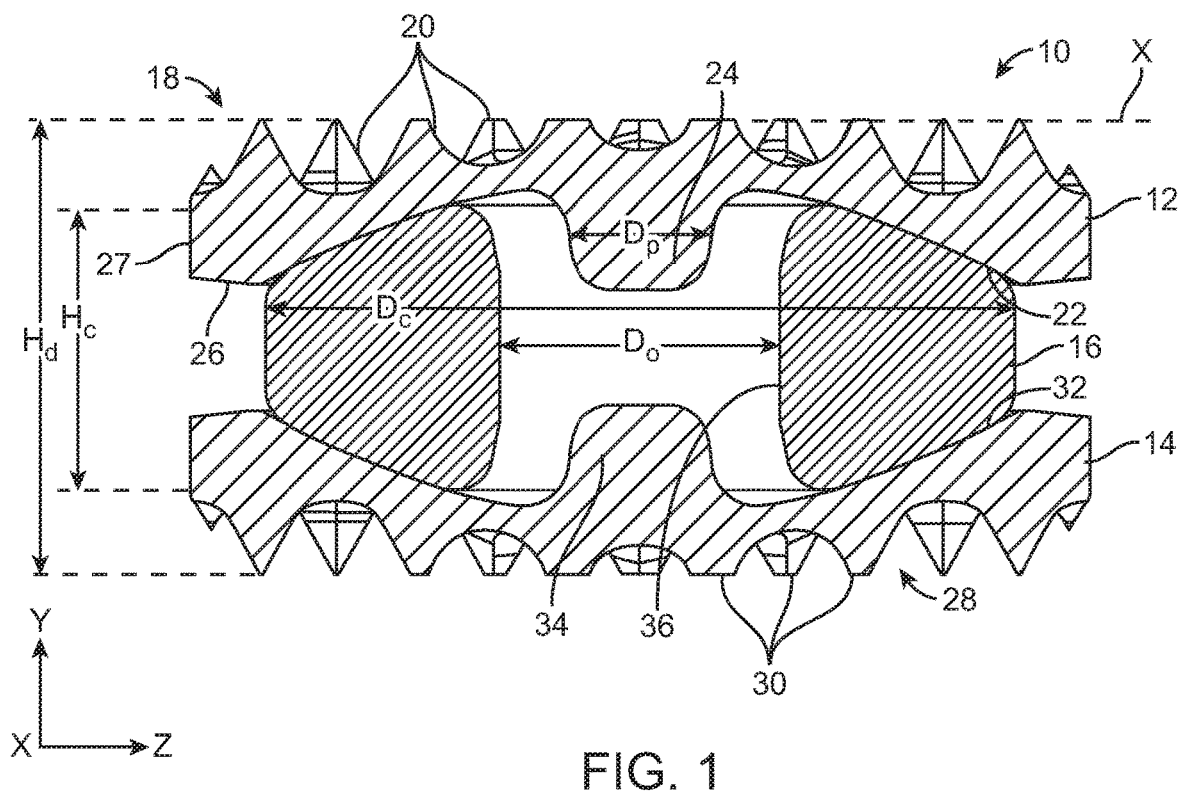
FIG. 1 is a cross-sectional view of a prosthetic disc in a neutral position.

Referring to FIG. 1 an intervertebral prosthesis 10 for insertion between adjacent vertebrae includes an upper plate 12, a lower plate 14 and a core 16. The core 16 is retained between the upper and lower plates 12, 14 by a retention feature in the form of central projections on the plates and an opening in the core 16. The retention feature is designed to allow the plates to slide over the upper and lower surfaces of the core in the anterior/posterior direction and in the lateral direction and to allow the plates to rotate with respect to each other and the core. The retention feature is also designed to prevent contact between the first and second plates during sliding movement of the plates over the core.

The upper plate 12 includes an outer surface 18 having a plurality of serrations 20 with serrations at outer portions of the plate having pyramid shapes and serrations at the inner portion of the plate having truncated pyramid shapes. Serrations between the outer and inner portions of the plate have been truncated to a lesser degree than the inner serrations. This variation in truncation allows the top of each of the serrations to lie in a single plane illustrated in FIG. 1 by the line X. The upper plate 12 has an inner bearing surface 22 with a concave spherical shape and a circular perimeter with a diameter $D_b$ (shown in FIG. 5). A central projection 24 extends from a center of the inner bearing surface 20 toward the lower plate 14. The central projection 24 is in the form of a substantially cylindrical peg having a diameter $D_p$ measured at substantially a midpoint of its height. The term substantially cylindrical as used herein means varying in diameter by less than 10 percent along at least 50 percent of a height or length. The upper plate 12 includes an annular perimeter surface 26 surrounding the inner curved bearing surface 22 on a bottom side of the plate. A lateral sidewall portion 27 extends around the plate 12 between the annular perimeter surface 26 and the outer vertebral body contacting surface 18.

The lower plate 14 has an outer surface 28 with a plurality of serrations 30 and an inner bearing surface 32 with a projection 34 extending upwards from the inner bearing surface. In the embodiment of FIG. 1, the lower plate 14 is identical to upper plate 12, however, in other embodiments the upper and lower plates can have different configurations to more closely match the anatomy of the patient. For example, the upper or superior plate may have a somewhat domed shaped outer surface to accommodate the anatomical concavity in the lower surfaces of the vertebrae. In addition, one or both of the upper and lower plates can be provided with non-parallel upper and lower surfaces to accommodate spinal lordosis. The advantages of identical upper and lower plates include the ease of manufacturing, assembly and insertion without need for checking orientation.

The core 16 is symmetrical with respect to a midline in each of three orthogonal dimensions. The central opening 36 of the core 16 has a smallest diameter $D_o$ which is larger than the diameter $D_p$ of the projections 24, 34. The diameter $D_p$ of the projections is measured at approximately a middle of the projection about half way between a top and bottom of the projection. The central projections 24, 34 each have a diameter $D_p$ of about 60% to 30% of a diameter $D_o$, about 65% to 40% of a diameter $D_o$, and preferably about one half or less of a minimum diameter $D_o$ of the central opening in the core 16. The core has an overall diameter $D_c$ which is substantially equal to the diameter $D_b$ of the concave bearing surfaces of the upper and lower plates. In one embodiment, the diameter $D_c$ of the core is about 95% to about 105% of the diameter $D_b$ of the bearing surface. Although the core 16 is illustrated with a central opening 36 extending through the height of the core, the central opening can also be a partial opening not extending fully through the core. The diameter $D_o$ of the central opening 36 of the core 16 is at least 30%, or preferably at least one third of a maximum diameter $D_c$ of the core.

The core 16 has a shape of an annular, flattened ring with a cross section through the wall of the ring having a substantially isosceles trapezoidal shape with rounded corners. The core cross section has a long base side at the edge of the central opening 36 and a short base side at the exterior cylindrical wall of the core. Upper and lower surfaces of the core form the angled sides of the trapezoidal cross section and are preferably identical. The core shape can also be described as a flattened torus shape. Inner and outer walls of the core are substantially cylindrical and upper and lower walls of the core are portions of a sphere. Alternatively, the core 16 can be described as a perforated lens. The top and bottom surfaces are spherical with spherical radii's matching those of the congruent endplate concavities 22, 32.

The core has a maximum height $H_c$ in the axial direction and a maximum diameter $D_c$ in the radial direction. In one embodiment, the maximum diameter $D_c$ is at least two times the maximum height $H_c$.

Figure 2:
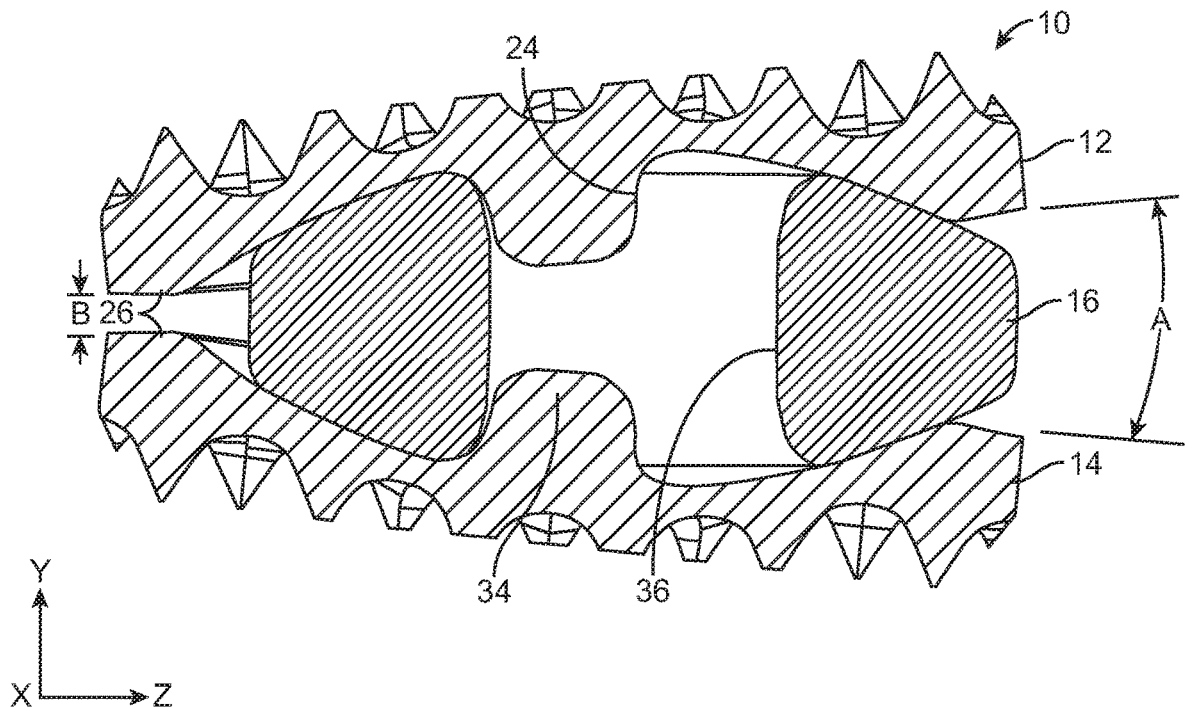
FIG. 2 is a cross-sectional view of the prosthetic disc of FIG. 1 is a maximum articulated position.
Figure 3:
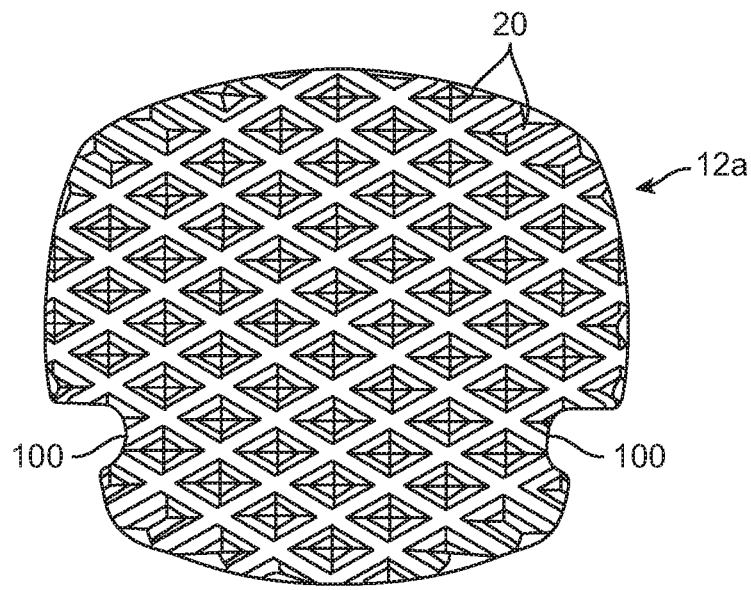
FIG. 3 is a top view of the prosthetic disc of FIG. 1.

FIG. 2 shows the intervertebral prosthetic disc at a maximum angle of articulation. At the maximum articulation, the projections 24, 34 abut the side walls of the opening 36 in the core and prevent further articulation. The core configuration as described and shown allows the upper and lower plates to articulate about the core at least 5 degrees and preferably about 6 degrees from a neutral position, shown in FIG. 1 in each of the anterior/posterior and lateral directions. The maximum articulation angle between the plates 12, 14 is the angle A, as shown in FIG. 2. The articulation angles A of 5 degrees and 6 degrees correspond to a total anterior/posterior or lateral articulation of about 10-12 degrees between endplates 12, 14. Preferably a maximum articulation angle A between the plates 12, 14 is less than 8 degrees in any direction for a total articulation of 16 degrees or less.

The central projections 24, 34 and central opening 36 cooperate with one another to retain the core between the plates and limit motion of the first and second plate with respect to one another to prevent contact between the annular perimeter surfaces 26 of the plates during sliding movement of the plates over the core. As shown in FIG. 2, a gap B between the annular perimeter surfaces 26 at a maximum articulation is preferably at least 0.5 mm. The prevention of contact between the plates 12, 14 significantly reduces metallic wear particulate generation in wear testing and in vivo which can be caused by rubbing contact between metallic plates. Preferably, the central projections 24, 34 and central opening 36 create both a retention feature to retain the core between the plates and a motion limiting feature to prevent contact between the annular perimeter surfaces 26 and between any other part of the plates 12, 14 during sliding movement of the plates over the core.

The assembled disc in the neutral configuration shown in FIG. 1 with the plates in a parallel orientation and the core positioned centrally has a height $H_d$ which can vary between 3.5 mm and 8 mm for a cervical disc and 8 and 15 mm for a lumbar disc. In a preferred embodiment of a cervical disc, the disc is provided in a range of heights including at least 3 different heights from 3.5 to 6 mm. For example, heights 4, 5 and 6 mm can be provided to accommodate different patient anatomies. The different height discs may each include the same core size and different plate heights. Alternatively, the same plate heights can be used for all sizes with different core heights, or both the heights of cores and plates can vary between sizes. In a preferred set of discs, at least one disc size has a maximum height between outer surfaces of the two plates of 5 mm or less to accurately match anatomical heights.

In a preferred embodiment, the total maximum disc height $H_d$ is less than 2 times a height $H_c$ of the core and more preferably, the core maximum height $H_c$ is 55% or more of the total disc height $H_d$.

Interchangeable cores can also be provided which provide the surgeon with options for providing more or less motion depending on the motion desired for a particular patient. In one example, a first core having a central opening 36 having a diameter $D_o$ of the core 16 of about two times a diameter of the central projection 24 provides standard 10-18 degree motion, while a second core having a central opening 36 having a diameter $D_o$ of about 1.5-1.8 times a diameter or the central projection 24 provides limited motion of 5-12 degrees. The cores may be interchangeable prior to implantation. Alternately, the cores may be interchanged after the initial surgery with a follow on surgery to increase or decrease motion without removing the upper and lower plates. In one embodiment, a set of parts is provided as a surgical set for assembling an intervertebral disc for implantation in a patient, the set of parts can include identical or different upper and lower endplates and a plurality of cores having the same spherical curvature of upper and lower core bearing surfaces and different central opening diameters $D_o$.

In one embodiment, the upper and lower plates are formed of a metallic material, such as but not limited to, cobalt chrome molybdenum, titanium, composites of metal and ceramic and/or the like. The bone contacting surfaces of the upper and lower plates can be roughened or treated such as by aluminum oxide blasting or coated, such as with pure titanium, HA (hydroxylapatite) coating, micro HA coating, and/or bone integration promoting coatings. Any other suitable metals or combinations of metals may be used as well as ceramic or polymer materials, and combinations thereof. The bearing surfaces can be uncoated or treated or coated, such as, coated with titanium nitride. In some embodiments, it may be useful to couple two materials together to form the inner surface and the outer surface of the plates. Any other suitable combination of materials and coatings may be employed in various embodiments of the invention.

The core can be formed of a low-friction material, such as biologically compatible polymers including polyethylene, PEEK, UHMWPE, Vitamin E stabilized UHMWPE, PLA, fiber reinforced polymers, ceramics, metals, composites or the like. In one example, the core can be formed of PAEK materials including neat (unfilled) PEEK, PEEK-OPTIMA available from Invibio, Inc., fiber reinforced PEEK, such as PEEK-CFR (carbon fiber reinforced) from Invibio, Inc., glass fiber reinforced PEEK, ceramic filled PEEK, Teflon filled PEEK, barium sulfate filled PEEK or other reinforced or filled PAEK materials.

According to one embodiment of the invention, the upper and lower plates are formed of titanium and the core is formed of polyethylene to provide a low wear metal on poly bearing without metal on metal contacting surface.

FIGS. 3-6 show a single upper or lower plate or a series of plates of differing sizes. As seen most clearly in the top view of FIG. 3 and the bottom view of FIG. 5, each of the plates has a pair of side notches 100 configured for grasping the plate with an insertion instrument. As shown in FIGS. 3-6, the side notches 100 are located toward the anterior side of the plates for grasping the plates on the anterior side of the disc and insertion from the anterior side of the spine. The insertion instrument (not shown) includes opposing jaws which fit into the two side notches 100. In one preferred embodiment, a single pair of opposition jaws is able to grasp both the upper and lower plates by engaging the upper and lower plates both with the same opposing right and left jaws. Once the upper and lower plates are assembled with the core there between and grasped by the insertion instrument, the upper and lower plates and core are held in a fixed configuration and not able to articulate until released from the jaws of the insertion instrument. In the constrained insertion configuration, the upper and lower plates can be parallel or slightly angled with the posterior edges of the plates closer to one another.

Figure 4:
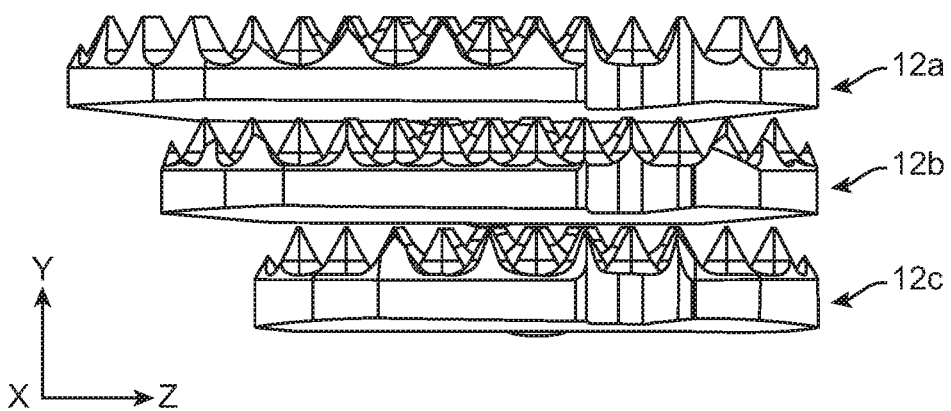
FIG. 4 is a side view of three different sizes of the upper endplate of the prosthetic disc of FIG. 1.
Figure 5:
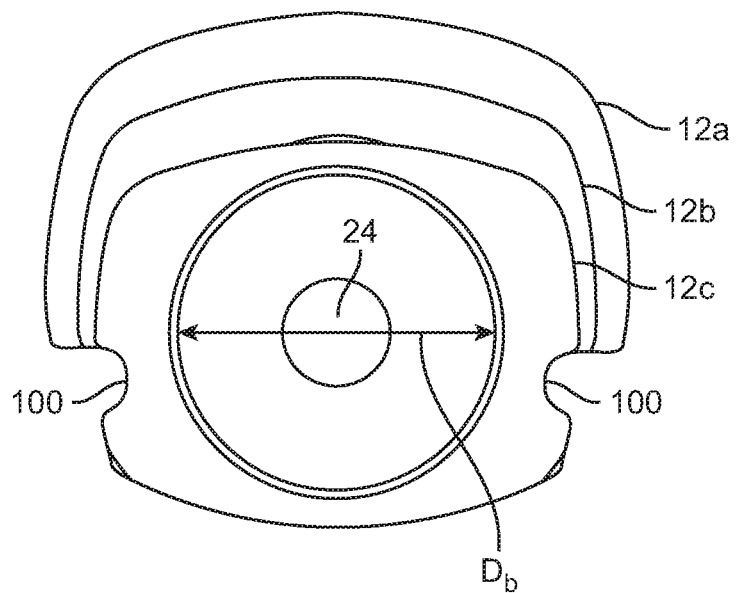
FIG. 5 is a bottom view of the three different sizes of the upper endplate of the prosthetic disc of FIG. 1.
Figure 6:
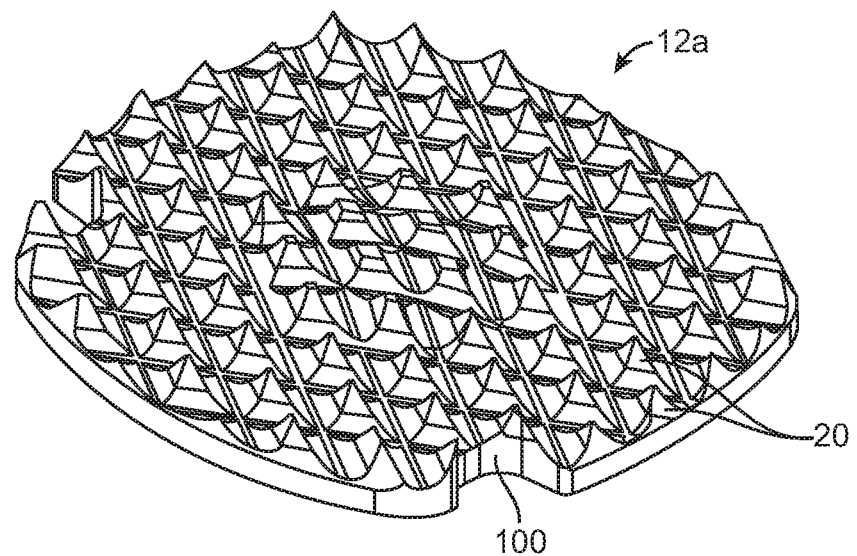
FIG. 6 is a perspective view of an upper endplate of the prosthetic disc of FIG. 1.

As shown in FIGS. 4 and 5, the discs may be provided in different sizes, such as large 12a, medium 12b and small 12c footprint sizes having different width and depth dimensions to fit different patients. For the purpose of using the same instrument to insert all of the different sizes, the shapes and sizes of the anterior side of each of the discs and the notches 100 are identical or at least have the same notches.

The serrations 20 have a pyramid shape. As shown in the top view of FIG. 3, the pyramid shaped serrations can be elongated in the lateral direction to provide improved plate securement in the anterior posterior direction. The anterior/posterior direction is the direction most likely to have plate migration. In one example, the ratio of anterior/posterior dimension to lateral dimension of the serrations is between about 2:3 to about 3:4.

In the embodiments shown, the pyramid shaped serrations have been included for improving fixation. However, other types of fixation may also be included in addition to or in place of the serrations, such as teeth or fins. For example, a single central fin can be provided on each of the plates extending in an anterior posterior direction with an angled posterior edge for aiding in insertion. Alternatively, two or more fins can also be provided on each plate. The fins can be configured to be placed in slots in the vertebral bodies or to be placed without cutting slots. In one example, a single fin can be provided on one plate while double fins can be symmetrically arranged on the other plate to achieve a staggered arrangement particularly useful for multi-level disc implant procedures. Multiple small fins can also be provided in an in-line orientation. In alternative embodiments, the fins may be rotated away from the anterior-posterior axis, such as in a lateral-lateral orientation, a posterolateral-anterolateral orientation, or the like for implantation in the associated directions.

Figure 7:
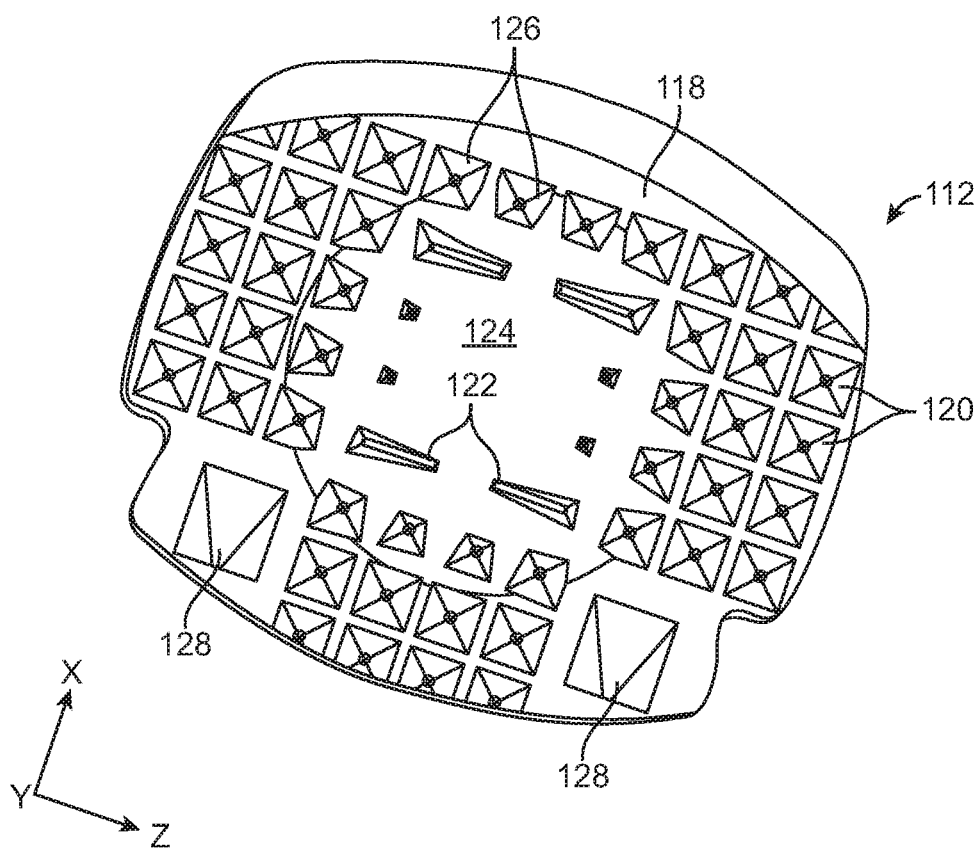
FIG. 7 is a top view of an alternative embodiment of an upper endplate of a prosthetic disc.
Figure 8:
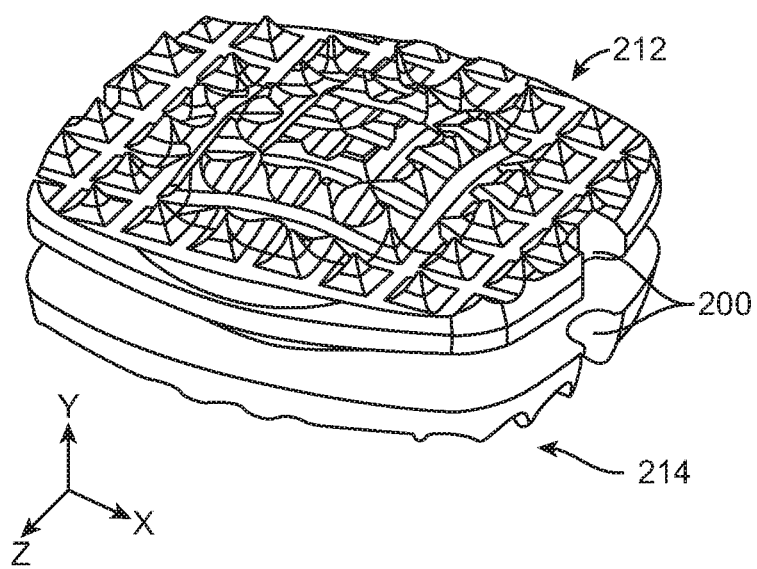
FIG. 8 is a perspective view of another alternative embodiment of a prosthetic disc.
Figure 9:
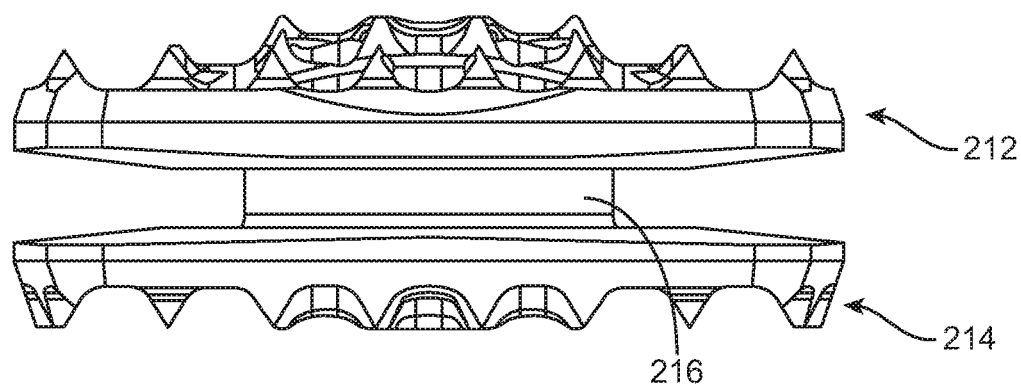
FIG. 9 is an anterior view of the prosthetic disc of FIG. 8.
Figure 10:
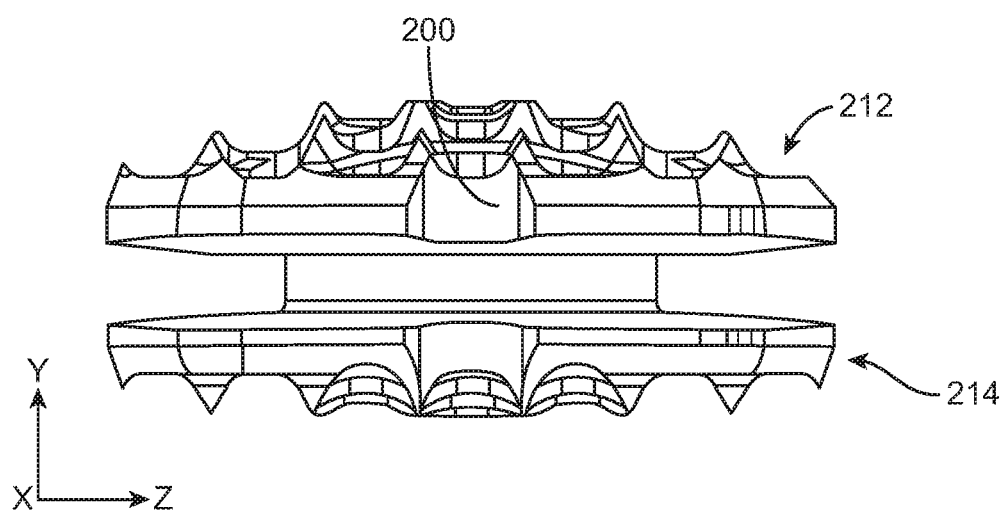
FIG. 10 is a lateral view of the prosthetic disc of FIG. 8.
Figure 11:
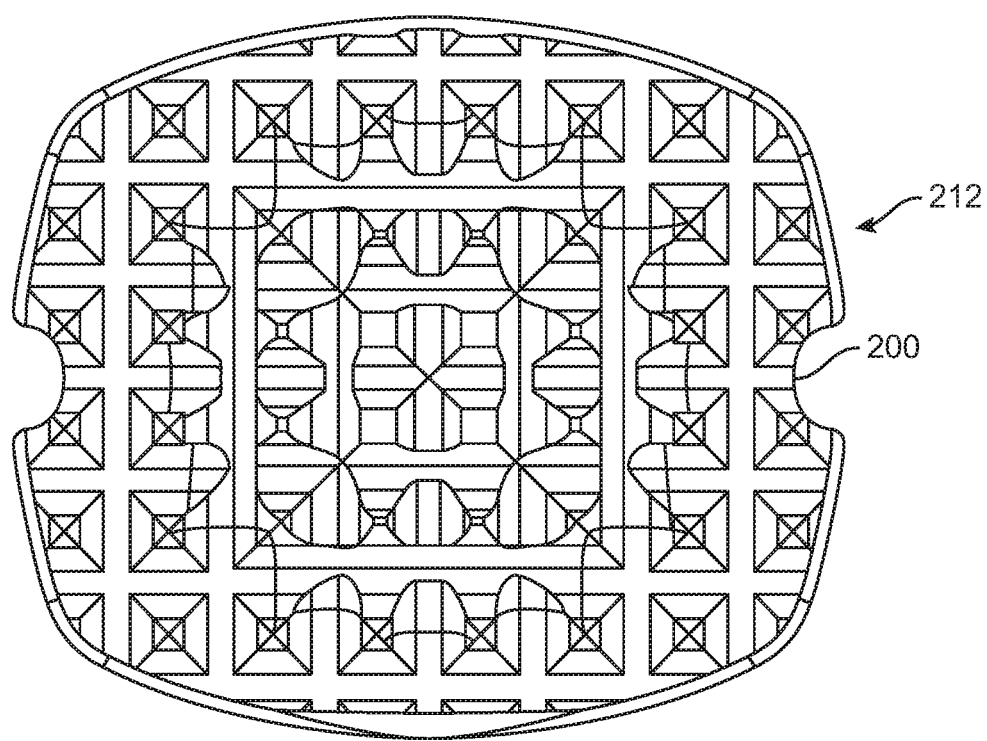
FIG. 11 is a top view of the prosthetic disc of FIG. 8.

FIG. 7 shows an alternative embodiment of an upper endplate 112 having a different configuration of projections on a bone contacting upper surface 118. A plurality of different shaped serrations are provided including symmetrical serrations 120 about the periphery of the disc, laterally elongated serrations 122 on a central dome 124, non-symmetrical serrations 126 around the periphery of the central dome, and serrations (or teeth) 128 with a vertical or near vertical anterior surface for additional fixation at the anterior side of the plate. The endplate 112 also has an anterior pair of side notches 100 configured for grasping the plate with an insertion instrument. Any one or more of these serrations types can be combined with the elongated pyramid shaped serrations 20 of the FIG. 1-6 embodiment.

FIGS. 8-11 show a further alternative embodiment of a pair of matching upper and lower plates 212, 214 positioned about a core 216. In this embodiment, a pair of side notches 200 configured for grasping the plate with an insertion instrument are positioned at a centered location between the anterior and posterior edges of the endplates. In this embodiment with centrally located notches 200, different size discs are inserted with different insertion instruments or the insertion instrument is adjustable to accommodate the different plate sizes. This embodiment has upper and lower plates 212, 214 which are identical and symmetrical and thus can be assembled without respect to top/bottom or anterior/posterior orientations.

Modification of the above-described assemblies and methods for carrying out the invention, combinations between different variations as practicable, and variations of aspects of the invention that are obvious to those of skill in the art are intended to be within the scope of the invention disclosure.

What is claimed is:

1. An intervertebral prosthesis for insertion between adjacent vertebrae, the prosthesis comprising:
    a first plate having an outer surface locatable against a respective vertebrae and an inner curved surface, wherein a first central projection extends from the inner curved surface;
    a second plate having an outer surface locatable against a respective vertebrae and an inner curved surface, wherein a second central projection extends from the inner curved surface toward the first plate;

a ring shaped core having a cross section with a trapezoidal shape, the core having upper and lower curved surfaces complementary in shape to the inner curved surfaces of the first and second plates to allow the plates to slide over the upper and lower surfaces of the core, and the core having a central opening configured to receive the first and second central projections;

wherein:

the upper curved surface and the lower curved surface of the core have spherical radii matching spherical radii of the inner curved surface of the first plate and the inner curved surface of the second plate, and the first and second central projections and the central opening cooperate with one another to retain the core between the first plate and the second plate and limit motion of the first plate and second plate with respect to one another to prevent contact between annular perimeter surfaces of the first plate and the second plate during sliding movement of the first plate and the second plate over the core.

2. An intervertebral prosthesis of claim 1, wherein the core has a maximum height in the axial direction and a maximum diameter in the radial direction and wherein the maximum diameter is at least two times the maximum height.

3. An intervertebral prosthesis of claim 1, wherein a diameter of the central opening of the core is at least one third of a maximum diameter in a radial direction of the core.

4. An intervertebral prosthesis of claim 1, wherein a maximum height of the intervertebral prosthesis in a neutral position with the first and second plates parallel and the core positioned between the plates is 5 mm or less.

5. An intervertebral prosthesis of claim 1, wherein the first and second plates are capable of articulating about the core at least 5 degrees from a neutral position in each of the anterior/posterior and lateral directions.

6. An intervertebral prosthesis of claim 1, wherein the first and second central projections and central opening cooperate with one another to retain the core between the plates and limit motion of the first and second plate with respect to one another to prevent contact between any part of the first and second plates during sliding movement of the plates over the core.

7. An intervertebral prosthesis of claim 1, wherein the core cross section has first and second curved outer corners and third and fourth curved inner corners and no additional corners.

8. An intervertebral prosthesis of claim 1, wherein the trapezoidal core cross section has a long base within the central opening and a short base on the exterior of the core.

9. An intervertebral prosthesis of claim 1, wherein the central opening in the core is a through opening.

* * * * *